(12) United States Patent
Koerzdoerfer et al.

(10) Patent No.: US 12,360,189 B2
(45) Date of Patent: Jul. 15, 2025

(54) ACQUISITION OF DATA OF AN EXAMINATION OBJECT BY MEANS OF MAGNETIC RESONANCE WITH IMPROVED TIME MANAGEMENT

(71) Applicant: Siemens Healthcare GmbH, Erlangen (DE)

(72) Inventors: Gregor Koerzdoerfer, Erlangen (DE); Mathias Nittka, Baiersdorf (DE); Peter Speier, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 982 days.

(21) Appl. No.: 17/032,732

(22) Filed: Sep. 25, 2020

(65) Prior Publication Data

US 2021/0096199 A1 Apr. 1, 2021

(30) Foreign Application Priority Data

Sep. 27, 2019 (EP) .................... 19199992

(51) Int. Cl.
*G01R 33/483* (2006.01)
*A61B 5/055* (2006.01)
*G01R 33/50* (2006.01)
*G01R 33/54* (2006.01)
*G01R 33/56* (2006.01)

(52) U.S. Cl.
CPC .......... *G01R 33/4835* (2013.01); *A61B 5/055* (2013.01); *G01R 33/50* (2013.01); *G01R 33/543* (2013.01); *G01R 33/5608* (2013.01)

(58) Field of Classification Search
CPC .. G01R 33/4835; G01R 33/50; G01R 33/543; G01R 33/5608; G01R 33/565; A61B 5/055

See application file for complete search history.

(56) References Cited

U.S. PATENT DOCUMENTS

2009/0245607 A1* 10/2009 Sugiura .............. G01R 33/3607
 382/131
2010/0289493 A1 11/2010 Stemmer
(Continued)

OTHER PUBLICATIONS

Nehrke, Kay et al. "DREAM—A Novel Approach for Robust, Ultrafast, Multislice B1 Mapping" Magnetic Resonance In Medicine; vol. 68; pp. 1517-1526, 2012 //DOI 10.1002/mrm.24158.
(Continued)

*Primary Examiner* — Rishi R Patel
(74) *Attorney, Agent, or Firm* — Banner & Witcoff Ltd.

(57) ABSTRACT

Techniques are disclosed for acquiring data of an examination object in at least two slices by means of a pulse sequence. Time intervals between excitations of neighboring slices and associated minimum intervals are determined. From these, time intervals to be adapted between excitations of neighboring slices are determined and adapted before a measurement protocol is executed, with the adapted time intervals. Through the determination of a minimum time interval between excitations of neighboring slices and the adaptation of the time intervals between excitations of neighboring slices, a falsification of measurement results can be avoided, measurement time of the chosen measurement protocol is not increased, and the user is not restricted in their choice of the slices to be excited.

20 Claims, 4 Drawing Sheets

(56) References Cited

U.S. PATENT DOCUMENTS

2015/0355304 A1* 12/2015 Kurokawa ........... G01R 33/543
                                                324/309
2016/0116557 A1   4/2016 Feiweier
2016/0178719 A1*  6/2016 Liu .................... G01R 33/4835
                                                324/309
2017/0205487 A1*  7/2017 Zeller ................ G01R 33/4835
2017/0227618 A1*  8/2017 Speier ................ G01R 33/4835
2017/0328971 A1* 11/2017 Bilgic ................ G01R 33/5611

OTHER PUBLICATIONS

European Search Report dated Apr. 3, 2020, Application No. 19199992.9.

* cited by examiner

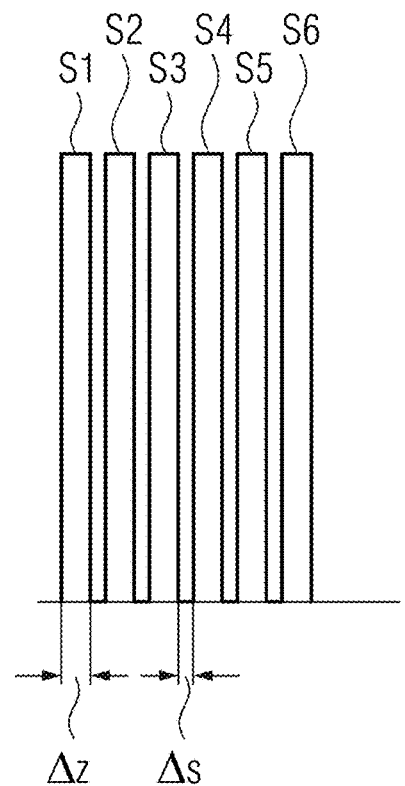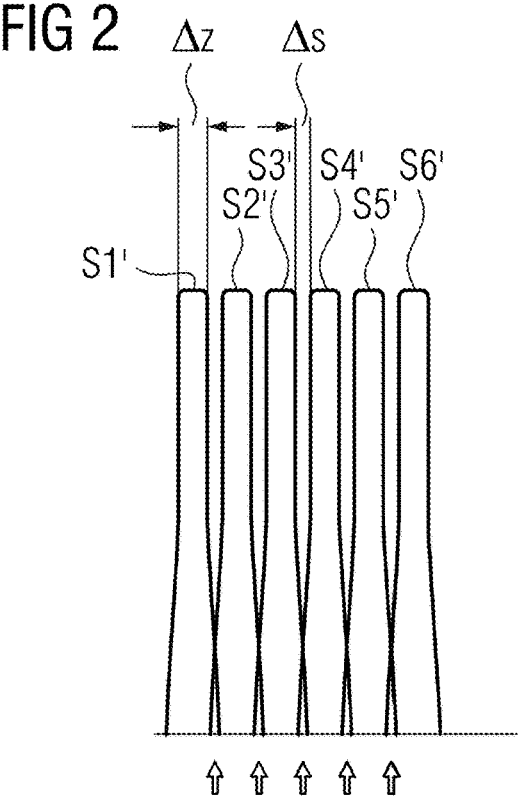

ACQUISITION OF DATA OF AN EXAMINATION OBJECT BY MEANS OF MAGNETIC RESONANCE WITH IMPROVED TIME MANAGEMENT

CROSS-REFERENCE TO RELATED APPLICATIONS

The present application claims the benefit of the filing date of European patent application no. EP 19199992.9, filed on Sep. 27, 2019, the contents of which are incorporated herein by reference in their entirety.

TECHNICAL FIELD

The present disclosure relates to techniques for the acquisition of data of an examination object by means of magnetic resonance with improved time management.

BACKGROUND

Magnetic resonance (MR) technology is a known technique with which images of the inside of an examination object can be created. Expressed in simple terms, the examination object is positioned for this process in a magnetic resonance device in a comparatively strong, static, homogeneous basic magnetic field, also called a B0-field, with field strengths of 0.2 Tesla to 7 Tesla or more, so that its nuclear spins orient themselves along the basic magnetic field. To trigger nuclear spin resonances radio-frequency excitation pulses (RF pulses) are radiated into the examination object, the triggered nuclear spin resonances are measured as so-called k-space data and, on the basis of said data, MR images are reconstructed or spectroscopy data is established. For spatial encoding of the measurement data, rapidly switched magnetic gradient fields are superimposed on the basic magnetic field. The recorded measurement data, also referred to for short as just data, is digitized and stored as complex numerical values in a k-space matrix. From the k-space matrix occupied by the values, e.g. by means of a multidimensional Fourier transformation, an associated MR image is able to be reconstructed.

SUMMARY

By means of a slice selective excitation by RF excitation pulses with a corresponding bandwidth and simultaneous switching of gradient fields in the slice selection direction, so-called slice selection gradients, only spins of a desired spatial layer in the examination object can explicitly be excited.

Shown in FIG. 1 are schematic ideal slice excitation profiles of such a slice selective excitation. By way of example, the diagram shows six slices S1, S2, S3, S4, S5 and S6, which each have an extent in the slice direction (a slice thickness) of $\Delta z$, which for example can lie in a range of between one millimeter and one centimeter, or possibly even more. In the example shown, the slices S1, S2, S3, S4, S5 and S6 are spaced apart from each other at a distance of $\Delta s$ in the slice direction. Depending on the application, this distance $\Delta s$ between the slices used can be selected to be more (e.g. greater than or equal to $\Delta z$) or less, equal to zero, or negative (e.g. so that the slices overlap).

In reality, however it is not possible to excite ideal slice excitation profiles with an ideal rectangular function (as shown in FIG. 1 for example). Since a real RF excitation pulse always has a finite bandwidth, a real slice excitation profile will never appear exactly rectangular. Shown schematically in FIG. 2 are real slice excitation profiles S1', S2', S3', S4', S5', and S6', which are similar to those shown in FIG. 1, and also have a slice thickness $\Delta z$ and a distance $\Delta s$ from one another. However, the real slice excitation profiles S1', S2', S3', S4', S5', and S6' diverge from one another in the lower area shown, so that the result is intersections (marked by thick arrows).

This means that, with each excitation of a slice, because of the finite bandwidth of the RF excitation pulse, there is also an excitation of the spins outside the slice, and thereby a magnetization of the spins in areas adjacent to the slice. This is referred to as the problem of slice crosstalk in slice selective MR measurements and, in particular, in MR imaging.

In MR measurements of a number of slices with a small distance $\Delta s$, this type of crosstalk can lead to the signal of a slice being influenced by a preceding excitation of a neighboring slice (this is also called a pre-saturation effect), which can lead to signal losses or changes in contrast.

The problem can principally be addressed by a user by choosing suitable recording parameters (e.g. adequate distances between slices $\Delta s$, or time intervals between the slice excitations). However, the knowledge necessary to do this (e.g. the slice excitation profiles of the RF excitation pulse used in each case) is not available to the user as a rule, or the physical relationships are not known. Therefore, it is unlikely that users are in a position to deal with this problem themselves.

It is also possible to prevent measurement parameters that may possibly be unfavorable through restrictions in the measurement software. For example, a minimum distance for the distance between slices $\Delta s$ can be enforced, e.g. 30% of the distance between slices $\Delta z$, which should prevent crosstalk or at least reduce it. However, this is often against the desires of a user, who possibly does not want any such gaps between the measured slices.

The underlying object of the disclosure, therefore, is to make possible slice selective MR measurements that avoid the disadvantages stated above.

The object is achieved as described in the claims and throughout the disclosure such as a method for acquisition of data of an examination object by means of magnetic resonance, a magnetic resonance apparatus, a computer program, and an electronically-readable data medium.

In an aspect, a method for acquisition of data of an examination object by means of magnetic resonance comprises:

Loading a measurement protocol for acquisition of data of an examination region of the examination object in at least two slices by means of a pulse sequence, Determining a time interval between excitations of neighboring slices carried out within the framework of the pulse sequence, Determining a minimum time interval between excitations of neighboring slices carried out within the framework of the pulse sequence on the basis of parameters from the group of pulse sequence parameters, tissue parameters of the examination region of the examination object from which data is to be acquired with the pulse sequence and selectable quality parameters, Establishing as time intervals to be adapted specific time intervals between excitations of neighboring slices carried out within the framework of the pulse sequence, which do not fall below the associated specific minimum time interval, Adapting the time intervals established that are to be adapted between excitations of neighboring slices carried out within the framework of the pulse sequence in such a way that none of the adapted time intervals between excitations of neighboring slices carried out within the framework of the adapted pulse sequence falls below the minimum time interval, Acquiring data of the examination object using an adapted pulse sequence, which contains the adapted time intervals.

One of the ideas underlying the disclosure is that not all slices are generally equally affected by crosstalk effects, for example edge slices. This can lead to especially disruptive signal jumps from slice-to-slice. When reference is made to neighboring slices, unless specified otherwise, this means slices located adjacent to one another, which are adjacent in such a way that an excitation of a magnetization in one slice, also leads to a magnetization of the neighboring slice.

The problem can have a more serious effect with quantitative imaging, when crosstalk effects falsify the quantitative parameter maps, in particular because the occurrence of the problem is not recognizable to the user if, for example, they change the sequence parameters (e.g. slice number or distance between slices).

The determination of a minimum time interval between excitations of neighboring slices carried out within the framework of the pulse sequence may be performed automatically, and an explicit, automatic, adaptation of only time intervals to be adapted between excitations of neighboring slices carried out within the framework of the pulse sequence, on the one hand enables a falsification of measurement results to be cleverly avoided, wherein on the other hand the measurement time of the selected measurement protocol is not unnecessarily increased, and the user is not inadvertently restricted in the choice of the slices to be excited.

In an aspect, a magnetic resonance apparatus is provided that comprises a magnet unit, a gradient unit, a radio frequency unit, and a control device with a distance determination unit embodied for carrying out the aspects of the method discussed herein.

In an aspect, a computer program is provided that implements the aspects of the method discussed herein on a control device when the computer program is executed on the control device.

The computer program can also be present in the form of a computer program product (e.g. a non-transitory computer-readable medium), which is able to be loaded directly into a memory of a control device, with program code means for carrying out the aspects of the method discussed herein when the computer program product is executed in the computing unit of a computer system.

In an aspect, an electronically-readable data medium is provided that comprises electronically-readable control information stored thereon, which comprises at least one computer program and is embodied in such a way that, when the data medium is used in a control device of a magnetic resonance apparatus, it carries out the aspects of the method discussed herein.

The advantages and versions specified with regard to the method also apply by analogy to the magnetic resonance apparatus, the computer program, and the electronically-readable data medium.

BRIEF DESCRIPTION OF THE DRAWINGS/FIGURES

Further advantages and details of the present disclosure emerge from the exemplary embodiments described below as well as with reference to the drawings. The examples given do not represent any restriction of the disclosure. In the figures:

FIG. 1 shows a schematic diagram of example ideal slice excitation profiles,

FIG. 2 shows a schematic diagram of example real slice excitation profiles, in accordance with one or more aspects of the present disclosure.

DETAILED DESCRIPTION

Figure 5:
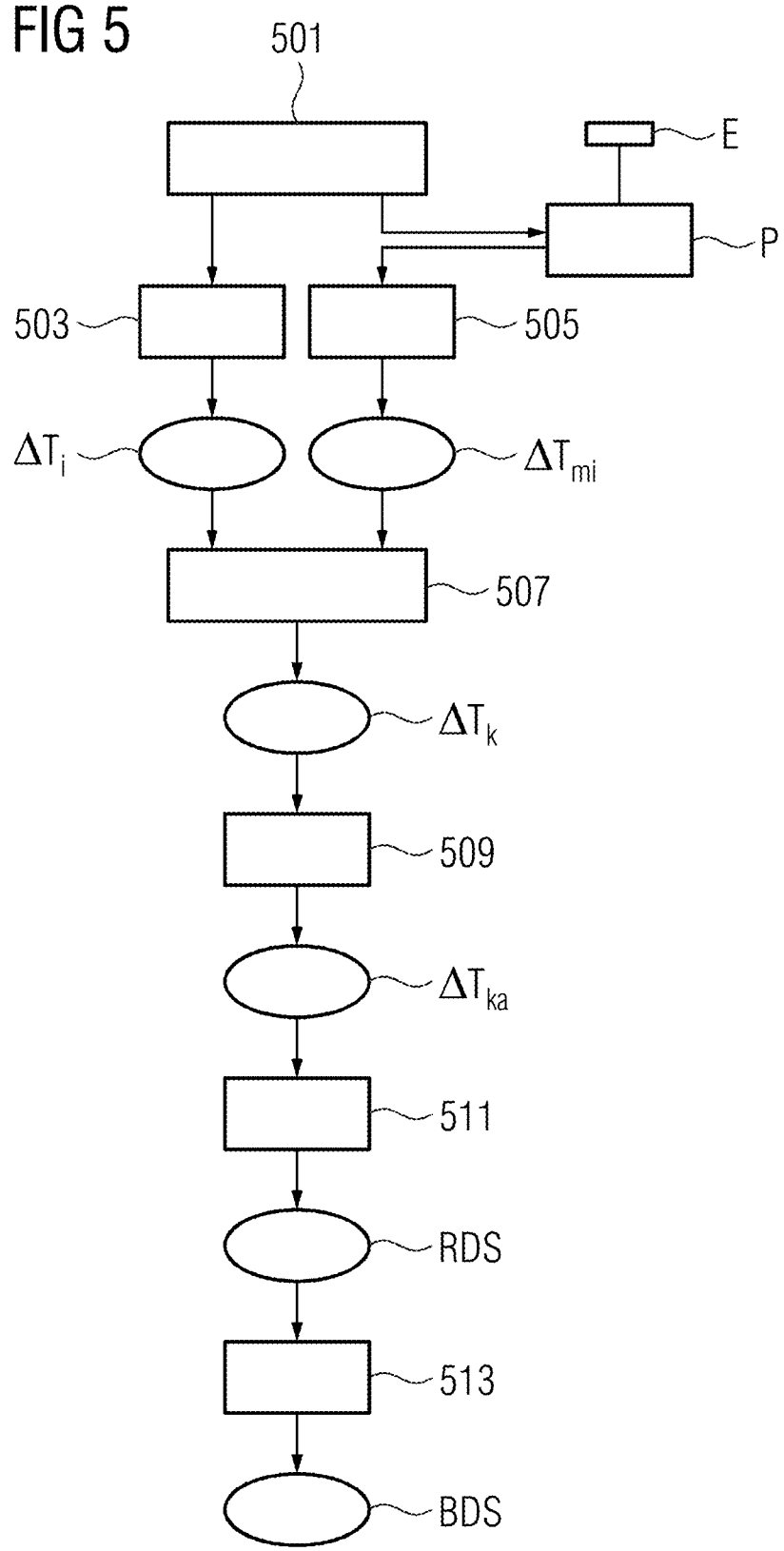
FIG. 5 shows a schematic diagram of an example flow diagram of a method, in accordance with one or more aspects of the present disclosure.

FIG. 5 is a schematic flow diagram of an example method for acquisition of data of an examination object by means of magnetic resonance.

In this method, a measurement protocol for acquisition of data of an examination region of the examination object in at least two slices by means of a pulse sequence is determined and/or loaded (block 501). Here, it is thus defined in particular from which examination region of the examination object, e.g. from which anatomical examination region (e.g. head, heart, liver, joint, whole body etc.) of a patient as examination object, in which slices data is to be acquired, and which pulse sequence is to be used.

A time interval $\Delta T_i$ between excitations of neighboring slices of the at least two slices carried out within the framework of the pulse sequence is determined (block 503). This can be done for example on the basis of pulse sequence parameters of the measurement protocol loaded, e.g. from a time sequence of excitations defined in the measurement protocol loaded. Here, the index i lies between one (the smallest possible number of such time intervals $\Delta T_i$) and the number of slices from which data is to be acquired, minus one (the largest possible number of such time intervals $\Delta T_i$). For example, if data is acquired from N slices by means of the method, the index i thus runs in integer steps from 1 to N−1.

Through the choice of the measurement protocol, and thus of the examination region, of the slices and of the pulse sequence, all time intervals $\Delta T_i$ between excitations of neighboring slices of the at least two slices carried out within the framework of the pulse sequence of the at least two slices can be read out directly from the planned measurement sequence of the loaded measurement protocol and can thereby be determined.

Moreover, a minimum time interval $\Delta T_{mi}$ (also referred to herein as a threshold time interval, as this may be associated with any suitable established threshold time interval value) between excitations of neighboring slices carried out within the framework of the pulse sequence is determined on the basis of parameters P from the group of pulse sequence parameters, tissue parameters of the examination region of the examination object, from which data is to be acquired with the pulse sequence, and selectable quality parameters (block 505). A time interval $\Delta T_i$, which reflects the amount of time between excitations of two neighboring slices within the framework of the pulse sequence, belongs here to a minimum time interval $\Delta T_{mi}$, which reflects the minimum time interval between the excitations of the same neighboring slices.

The minimum time interval $\Delta T_{mi}$ is determined in such a way that artifacts, e.g. crosstalk artifacts caused by slice crosstalk, are avoided or at least reduced in the acquisition of the data. On the basis of the determined minimum time interval $\Delta T_{mi}$, it can be established whether significant crosstalk effects are to be expected between two or more slices of the at least two slices.

During the determination of a minimum time interval $\Delta T_{mi}$ between excitations of neighboring slices carried out within the framework of the pulse sequence, a maximum value for a longitudinal relaxation time T1 of tissue present in the examination region to be examined and excited in the acquisition of the data can be assumed as the tissue parameter. This ensures that any magnetization created by an excitation of a slice before excitation of an adjacent slice has decayed. For example, a maximum longitudinal relaxation time T1 can be estimated conservatively as the longest longitudinal relaxation time T1 of any tissue that might be present in the examination region that will be excited during an excitation. For tissue occurring in a human or animal patient, around 3 seconds can thus be chosen for example as the value for a maximum longitudinal relaxation time.

It is also conceivable to determine a maximum longitudinal relaxation time on the basis, for instance, of the loaded measurement protocol and/or the examination region from which data is to be acquired, and e.g. using values already stored for longitudinal relaxation times. Here, for instance, the tissue that is present in the examination region can be determined on the basis of the examination region, e.g. using a previously stored assignment of tissue to examination regions in which the tissue occurs. On the basis of the loaded measurement protocol, in addition or as an alternative, it can be determined what tissue will be excited in the examination region. A longitudinal relaxation time T1 assigned to tissue determined in one of these ways can, for example, likewise be present stored beforehand (e.g. as typical longitudinal relaxation time T1 of the respective tissue), or as maximum longitudinal relaxation time T1 of the respective tissue, or also as a range of possible longitudinal relaxation times T1 of the respective tissue to determine a maximum longitudinal relaxation time T1 as a function of the measurement protocol and/or of the examination region, e.g. by establishing the longest longitudinal relaxation time T1 of the tissue determined.

Such a determination of a maximum longitudinal relaxation time T1 can thus be done automatically, wherein relevant tissue can be determined on the basis of the loaded measurement protocol and/or on the basis of the examination region, and using already stored assignments of longitudinal relaxation times T1 to possible tissues, a maximum longitudinal relaxation time T1 can be determined automatically.

It is also possible for a user to freely select the maximum longitudinal relaxation time T1 and to define it by an input E as a parameter P. However, the user should have sufficient knowledge to be able to make a sensible choice.

The parameters for the determination of a minimum time interval $\Delta Tmi$ between excitations of neighboring slices carried out within the framework of the pulse sequence can, additionally or as an alternative, comprise as a pulse sequence parameter a slice excitation profile of the RF excitation pulses used to excite the slices. On the basis of the slice excitation profiles of the RF excitation pulses used for excitation of the slices able to be determined from the pulse sequence included in the loaded measurement protocol, an ideal slice interval can be determined that should be present between neighboring slices to prevent crosstalk artifacts or to reduce them to a desired level (see also below in relation to quality parameters). Furthermore, a magnetization value can be established from slice excitation profiles, which specifies how strong a magnetization in a slice can be when a neighboring slice is excited.

The parameters for the determination of a minimum time interval between excitations of neighboring slices carried out within the framework of the pulse sequence, in addition or as an alternative, can comprise as a quality parameter a value for a maximum allowable pre-saturation of a magnetization of one of the slices before its excitation, e.g. as a percentage value. For example, maximum pre-saturation of the longitudinal magnetization of e.g. 1% to 3%, 10% to 20%, etc. or even more can be predetermined as a quality parameter. The selection of a maximum pre-saturation can take place depending on the application, for example. In this case, higher values for the pre-saturation can be more tolerable, for example, for a qualitative MR measurement than for quantitative MR measurements, such as MRF, for example. If in an application a contrast of a tissue type with a long longitudinal relaxation time T1, e.g. a fluid contrast (fluids have comparatively long longitudinal relaxation times T1), is only of secondary importance, the maximum pre-saturation can be chosen correspondingly larger. If, however, small changes in contrast in a tissue type with a long longitudinal relaxation time T1 are decisive for the application, the maximum pre-saturation should be correspondingly small, e.g. limited to approx. 1% to possibly 3%.

Such quality parameters enable a greater flexibility to be achieved, in particular the data can be acquired, if the highest quality able to be achieved is not required for an application, in a shorter time and in this case still with an acceptable quality. The quality parameter can be predetermined (automatically) for example application-specifically, e.g. as a function of the measurement protocol loaded.

It is also possible for a user to predetermine the quality value in line with their needs by an input E. Parameters for the determination of a minimum time interval between excitations of neighboring slices carried out within the framework of the pulse sequence can thus be chosen by a user for an acquisition of data of the examination object, e.g. via inputs E.

Parameters for the determination of a minimum time interval between excitations of neighboring slices carried out within the framework of the pulse sequence can however, in addition or as an alternative, also be predetermined, e.g. held in a memory for retrieval. The predetermined parameters can be estimated from values given in the literature or otherwise known.

Time intervals $\Delta T_i$ between excitations of neighboring slices carried out within the framework of the pulse sequence, which are shorter in each case than their associated minimum time interval $\Delta Tmi$ determined, can be determined as time intervals $\Delta T_k$ to be adapted (block 507). Through the determination of time intervals $\Delta T_k$ to be adapted, it is ensured that only time intervals $\Delta T_i$ that also need adapting are actually adapted, to avoid artifacts.

The index k runs from the value one, for a first time interval to be adapted, to the last time interval determined, i.e. likewise up to a maximum of N−1.

Established time intervals $\Delta T_k$ to be adapted between excitations of neighboring slices carried out within the framework of the pulse sequence can be adapted to adapted time intervals $\Delta T_{ka}$ in such a way that none of the adapted time intervals $\Delta T_k$ between excitations of neighboring slices carried out within the framework of the pulse sequence fall below the associated determined minimum time interval $\Delta T_{mi}$ of the respective neighboring slices.

In a simple case, the adaptation of a time interval $\Delta T_k$ determined that is to be adapted can be a lengthening of the time interval $\Delta T_k$ determined to at least the associated minimum time interval $\Delta T_{mi}$ determined, so that the following example applies:

$\Delta T_{mi} \leq \Delta T_k + T_w = \Delta T_i + T_w = \Delta T_{ka}$, wherein a time interval $\Delta T_i$ determined as a time interval $\Delta T_k$ to be adapted is lengthened by a wait time $T_w$, so that at least the associated minimum time interval $\Delta T_{mi}$ is reached as the adapted time interval $\Delta T_{ka}$.

The data to be acquired of the at least two slices can, for example, be measured in turn, measured completely for each slice in each case. The type of acquisition of the data is defined by the measurement protocol comprising the pulse sequence. A rough schematic diagram of a section of such a pulse sequence is reproduced in FIG. 3.

Figure 3:
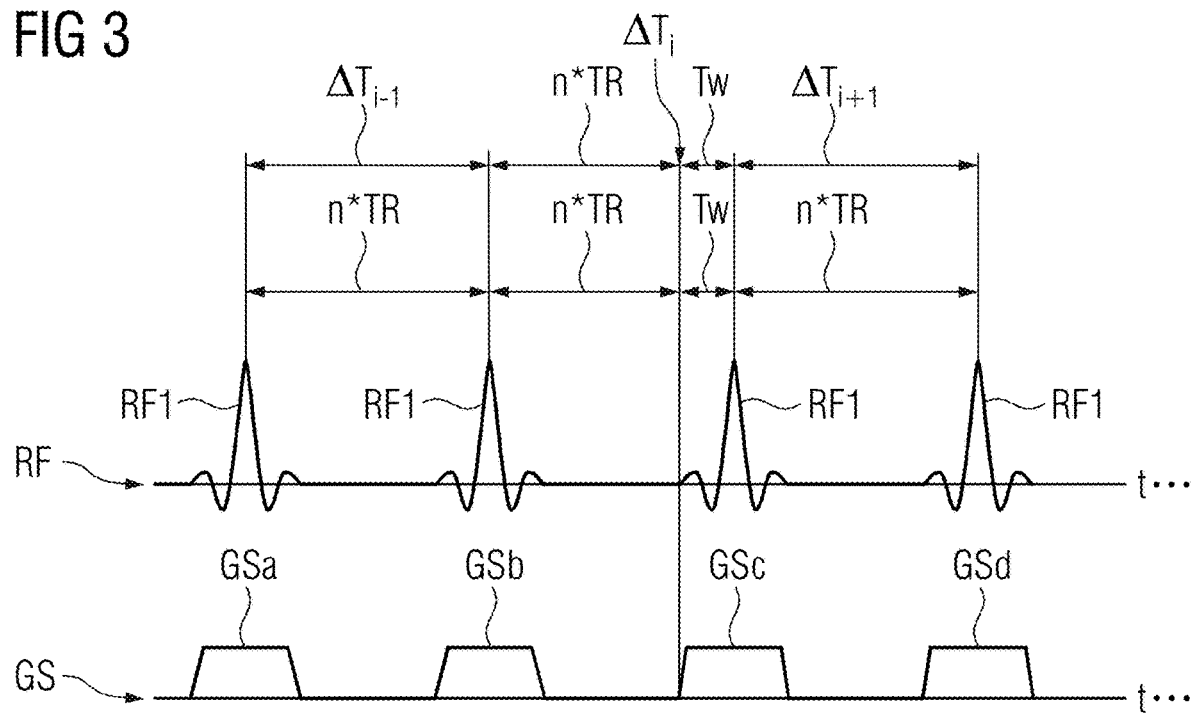
FIGS. 3 and 4 show schematic diagrams of example sections of simplified pulse sequences, in accordance with one or more aspects of the present disclosure.

Shown schematically in FIG. 3, in a line RF, over the course of time t, is the time sequence of RF excitation pulses radiated in (i.e. transmitted) one after another, as can take place in a sequential multi-slice measurement. A sequential multi-slice measurement thus records the slices to be recorded one after another.

While an RF excitation pulse RF1 is transmitted, a gradient GSa, GSb, GSc, and GSd in the slice selection direction GS is switched, with its timing matched to the pulse in each case, to create an excitation of the spins and thus a magnetization of the spins in a slice corresponding to the respective RF excitation pulse RF1 and the respective gradient GSa, GSb, GSc, and GSd in slice selection direction GS. In the example shown, the RF excitation pulses RF1 switched at the same time as the gradients GSa, GSb, GSc, and GSd in the slice selection direction GS each have a different (mid) frequency, so that in each case another of the four slices S1, S2, S3, and S4 is excited, wherein for example the RF excitation pulse RF1 transmitted with the gradient GSa encodes a slice S1, the RF excitation pulse RF1 transmitted with the gradient GSb encodes a slice S3, the RF excitation pulse RF1 transmitted with the gradient GSc encodes a slice S2, and the RF excitation pulse RF1 transmitted with the gradient GSd encodes a slice S4. In the example shown in FIG. 3, all gradients GSa, GSb, GSc, and GSd have the same amplitude in the slice selection direction GS, which represents the usual case that, for all slices RF to be encoded excitation pulses RF' with the same excitation bandwidth are used. In general, however, it would be possible for each slice to work with different bandwidths or even with different excitation profiles of the respective RF excitation pulse RF'.

In the diagram shown by way of example, the slices are excited one after the other in the sort order S1-S3-S2-S4, which represents a usual sort order, in accordance with which, of the consecutively numbered slices, data is first of all acquired from all odd-numbered slices and then data from all even-numbered slices. In accordance with a loaded measurement protocol that records data by means of a sequential multi-slice measurement, the respective excitations would usually be spaced apart in time by the excitation pulse RF1, and the number n of the echo signals to be recorded per slice in accordance with the repetition TR.

For example, with a repetition time TR of 10 ms and n=1000 as data of echo signals to be recorded per slice, a measurement time of 10 s per slice, and thus time intervals between (directly) spatially adjacent neighboring slices, for the example shown in FIG. 3 of $\Delta T_{i-1}=10$ s (between the slices S1 and S3, since the last excitation of slice S1 is followed by an excitation of the slice S3, which is not a directly adjacent slice) is produced, and $\Delta T_{i+1}=10$ s (between the slices S2 and S4, since the last excitation of slice S2 is followed by an excitation of the slice S4, which is not a directly adjacent slice), and $\Delta T_i=0$ s (between the slices S3 and S2, since the last excitation of slice S3 is followed by an excitation of the slice S2, which is a directly adjacent slice).

If a minimum time interval of $\Delta T_{mi}$, such as for example 12 s, has been determined for slices S2 and S3, the time interval $\Delta T_i = \Delta T_k$ to be adapted can be adapted here, for example, by a wait time $T_w$ being inserted, which corresponds at least to the associated minimum interval $\Delta T_{mi}$ determined ($T_w \geq \Delta T_{mi}$), to the associated minimum interval $\Delta T_{mi}$ determined ($T_w = \Delta T_{mi}$), between the last excitation of the slice S3 and the first excitation of the slice S2. Through this the time interval, $\Delta T_i$ will be lengthened by the wait time $T_w$.

In this way, for example, the adaptation of a specific time interval $\Delta T_k$ to be adapted between excitations of neighboring slices carried out within the framework of the pulse sequence can comprise an insertion of a wait time $T_w$ between the repetitions of the pulse sequence, in which one of the neighboring slices is excited in each case, of which the excitation has a time interval $\Delta T_k$ to be adapted.

The wait time $T_w$ is selected here in such a way that, by insertion of the wait time in a time interval to be adapted of excitations of neighboring slices, the time interval of the excitations of the neighboring slices is adapted in such a way that the adapted time interval of the excitations of the neighboring slices is increased to at least the associated minimum interval, to the associated minimum interval.

Figure 4:
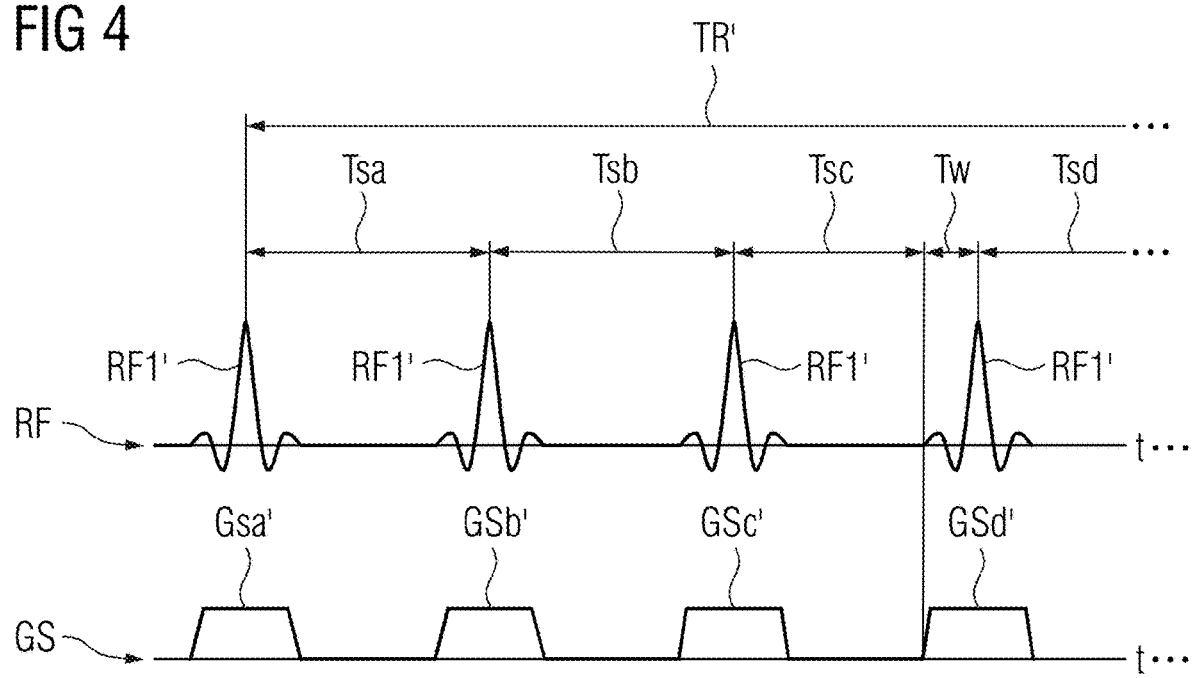

It is also conceivable to acquire the data of the at least two slices to be acquired at least partly within a repetition of the pulse sequence with an overall length of one repetition time, as occurs for example within the framework of an interleaved multi-slice measurement. A schematic diagram of a section of such a pulse sequence is reproduced in FIG. 4. Here for example, within a repetition time TR', one echo signal of a slice can be created in each case by slice selective excitations occurring one after another by radiating-in (i.e. transmitting) RF excitation pulses RF1' while simultaneously switching corresponding gradients GSa', GSb', GSc', GSd' in the slice selection direction GS and acquired as data. For the slice selective excitation by means of the RF excitation pulses RF' and the gradients GSa', GSb', GSc', GSd' in the slice selection direction GS, the same applies as stated with regard to FIG. 3. If, for example, data is to be acquired from six slices S1 to S6 in this way, the RF excitation pulse RF1' transmitted with the gradient GSa' encodes the slice S1, the RF excitation pulse RF1' transmitted with the gradient GSb' encodes the slice S3, the RF excitation pulse RF1' transmitted with the gradient GSc' encodes the slice S5, the RF excitation pulse RF1' transmitted with the gradient GSd' encodes the slice S2, and further gradients not shown with associated RF excitation pulses can encode the slices S4 and S6 for example.

If six (N=6) such slices S1 to S6 are measured with a repetition time TR of 12 s, for example, for such a measurement protocol loaded excitation time intervals Tsa, Tsb, Tsc, Tsd between slices excited consecutively one after another in a time of, in each case TR/"number of slices" are usually produced, i.e. in the example given for example Tsa=Tsb=Tsc=Tsd=Ts=12 s/6=2 s, to evenly fill the repetition time TR available within a repetition.

Depending on how the order in which the slices S1 to S6 are to be excited is sorted, the time intervals ΔTi of excitations of directly neighboring slices are thus produced initially as multiples of the above-mentioned excitation time interval Ts (v*Ts, with v=1 ... N−1). In the example shown, with a sorting of the slices to be excited one after another in accordance with the procedure described above in accordance with S1-S3-S5-S2-S4-S6, the following values are thus produced for the time intervals $\Delta T_i$ of excitations of directly neighboring slices:

Tsa+Tsb+Tsc=3*Ts, for the time interval of the excitations of the slices S1 and S2, Tsb+Tsc=2*Ts, for the time interval of the excitations of the slices S2 and S3, Tsb+Tsc+Tsd=3*Ts, for the time interval of the excitations of the slices S3 and S4, and similarly 2*Ts, for the time interval of the excitations of the slices S4 and S5, and 3*Ts, for the time interval of the excitations of the slices S5 and S6.

If a minimum time interval $\Delta T_{mi}$ of 5 s has been set for two slices for example (e.g. the slices S2 and S3), which in our example above with Ts=2 s, is thus longer than ΔTi(S2, S3)=2*Ts=4 s, a wait time $T_w$ e.g. of at least the length $\Delta T_{mi} - \Delta T_i = 5$ s−4 s=1 s between the excitations of the slices involved S2 and S3, thus here e.g. before the excitation of the slice S2 by the RF excitation pulse RF1', during which the gradient GSd' is switched, can be inserted to lengthen the time interval $\Delta T_k = \Delta T_i(S2, S3)$ to be adapted by the wait time $T_w$ to at least the associated minimum time interval $\Delta T_{mi}$ ($\Delta T_i + T_w \geq \Delta T_{mi}$).

Thus, the adaptation of a specific time interval $\Delta T_k$ to be adapted of excitations of neighboring slices can comprise an insertion of a wait time $T_w$ within a repetition of the pulse sequence between the excitations of the neighboring slices.

It has been assumed here for sake of simplicity and ease of explanation that an individual part measurement, i.e. an acquisition of the data of an echo signal of a slice, is negligibly short (e.g. a few milliseconds). If the acquisition of the data takes a length of time that is no longer negligible, this period of time should be applied to the wait time $T_w$ as well.

Thus, in general a wait time $T_w$ can be inserted after a time interval $\Delta T_k$ to be adapted in such a way that the time interval $\Delta T_k + T_w$ to be adapted lengthened in this way by the wait time $T_w$ does not fall below the associated minimum time interval $\Delta T_{mi}$, preferably so that the time interval $\Delta T_k + T_w$ to be adapted lengthened by the wait time corresponds to the associated minimum time interval $\Delta T_{mi}$. Thus, by the insertion of the described wait times $\Delta T_w$, a sufficient relaxation of the magnetization in the spatial region guarantees a subsequent excitation of a slice, and thus crosstalk artifacts are avoided. Since wait times $T_w$ are only determined and inserted for time intervals $\Delta T_k$ to be adapted, the overall measurement time is not increased unnecessarily, but only in cases in which there is a requirement for a desired freedom from artifacts to be achieved.

By an insertion of the wait time $T_w$ described above, a re-sorting of the time sequences in which the at least two slices will be excited is not necessary, so that other complications which might possibly arise through the re-sorting can be avoided. The insertion of a wait time $T_w$ represents only a minimal intervention into the course of the pulse sequence. No iteration is necessary for such an adaptation of the time intervals, but an adaptation of time intervals to be adapted by insertion of a wait time is possible without any great computational effort, so that the adapted time intervals can be quickly determined to be able to acquire data as free from artifacts as possible.

In an aspect, a method makes possible the automatic determination of wait times $T_w$, which can be inserted within a pulse sequence included in a loaded measurement protocol, to avoid disruptions caused by slice crosstalk, for example.

In addition or as an alternative, it is also possible for the adaptation of the determined time interval $\Delta T_k$ that is to be adapted to comprise a re-sorting of a chronological sequence in which the at least two slices are excited, one after another within the framework of the pulse sequence. A time interval between the excitations of the two spatially neighboring slices is likewise changed by the re-sorting. In the ideal case, it is possible to arrange all slices from which data is to be acquired in such a way that the time intervals between the excitations of spatially neighboring slices keep to the minimum time interval determined. In any event, the re-sorting can lead to other complications, such as eddy current effects, for example, and finding such an ideal sorting can be time-consuming. In order to ensure that after a re-sorting of the excitations of the at least two slices, a time interval $\Delta T_i$ that previously did not have to be adapted has not become a time interval $\Delta T_k$ to be adapted after a re-sorting, a pass of the method (block 501) should be started again. In this way, an ideal sorting can be found iteratively.

By using an adapted pulse sequence, which adheres to the adapted time intervals, data RDS of the at least two slices is acquired in accordance with the measurement protocol loaded (block 511).

From the acquired data RDS, by means of a Fourier transformation, for example, image data BDS of at least one of the at least two slices can be reconstructed (block 513).

Figure 6:
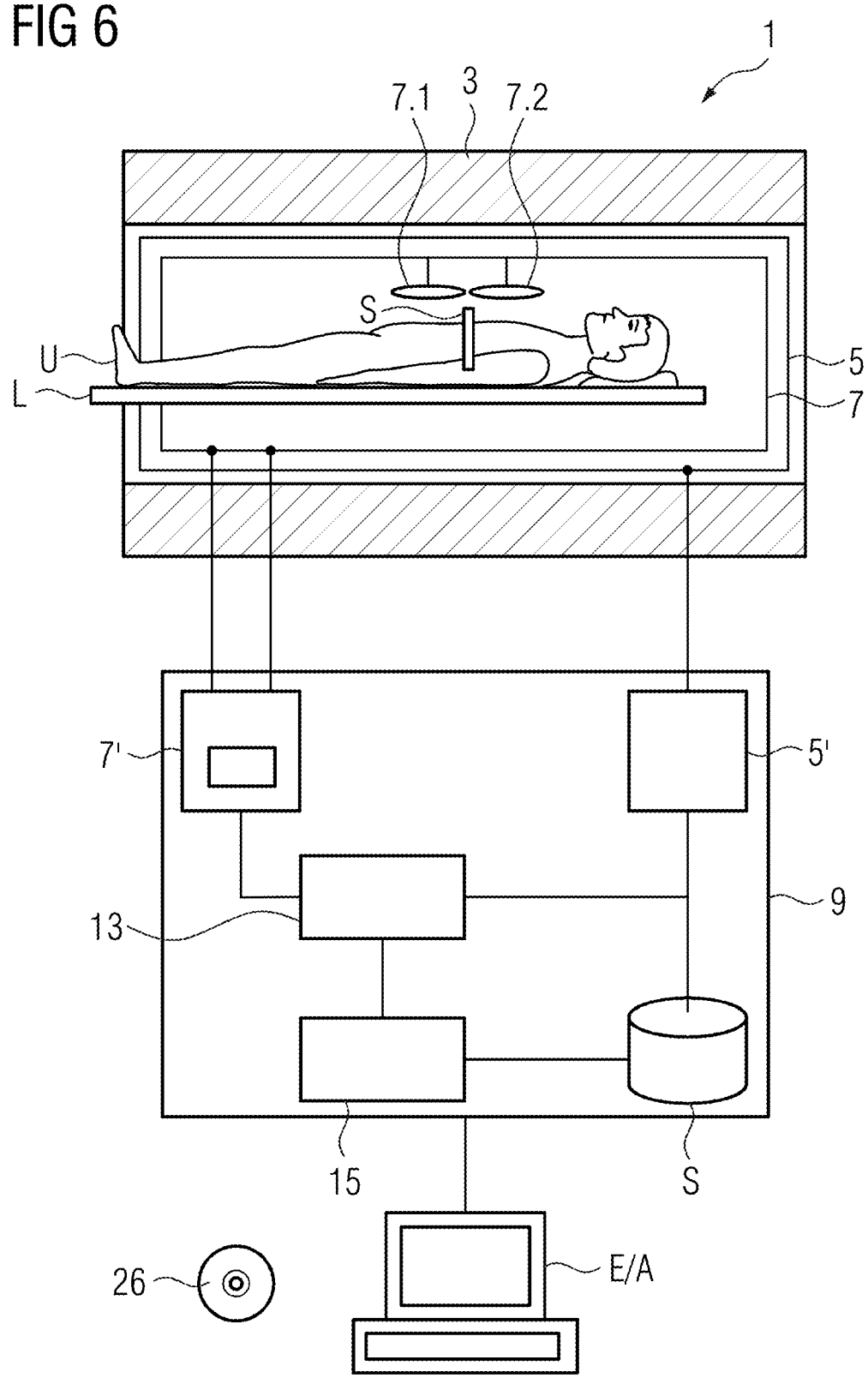
FIG. 6 shows a schematic of an example magnetic resonance apparatus, in accordance with one or more aspects of the present disclosure.

FIG. 6 shows a schematic of an inventive magnetic resonance apparatus 1. This comprises a magnet unit 3 for creating the basic magnetic field, a gradient unit 5 for creating the gradient fields, a radio frequency unit 7 for radiating in and for receiving radio-frequency signals, and a control device 9 (also referred to herein as a controller, processing circuitry, or a control computer) configured to perform the aspects of the methods discussed herein.

In FIG. 6, these subunits of the magnetic resonance apparatus 1 are only shown schematically. In particular, the radio frequency unit 7 may comprise a number of subunits, for example of a number of coils such as the coils 7.1 and 7.2 shown schematically or more coils, which can be designed either just for transmitting radio-frequency signals, for receiving the triggered radio-frequency signals, or for both.

For examination of an examination object U, for example of a patient or also of a phantom, said object can be introduced on a couch L into the magnetic resonance apparatus 1 into its measurement volume. The slice S represents an example of a target volume of the examination objects, from which data is to be recorded and thus acquired.

The control device 9 may be configured to control the magnetic resonance apparatus 1 and may control the gradient unit 5 by means of a gradient control 5' and the radio frequency unit 7 by means of a radio frequency transceiver control 7'. The radio frequency unit 7 can comprise a number of channels on which signals can be transmitted and received.

The radio frequency unit 7 is responsible, together with its radio frequency transceiver control 7', for the creation and the radiating-in (transmission) of a radio-frequency alternating field for manipulation of the spins in a region to be manipulated (for example in slices S to be measured) of the examination object U. In this process, the mid frequency of the radio-frequency alternating field, also referred to as the B1 field, is set as a rule where possible so that it lies close to the resonant frequency of the spins to be manipulated. Deviations from the mid frequency are referred to as off-resonance. For creating the B1-field, controlled currents are applied to the RF coils in the radio frequency unit 7 by means of the radio frequency transceiver control 7'.

The control device 9 further comprises a distance determination unit 15, with which in accordance with the aspects described herein time intervals and/or minimum time intervals can be determined. The control device 9 may be implemented as any suitable number of processors, processing circuitry, computers, etc., to facilitate execution of the aspects of the method as discussed herein.

A computing unit 13 (e.g. one or more processors of processing circuitry) included in the control device 9 may be configured to carry out all the computing operations needed for the requisite measurements and determinations. Intermediate results, and results needed or established here, can be stored in a memory unit S of the control device 9. The units shown are not to be understood absolutely here as physically separate units, but merely represent a subdivision into logical units, which can also be realized as fewer, additional, or alternate units (e.g. as one single physical unit).

Via an input/output device E/A of the magnetic resonance apparatus 1, control commands can be directed to the magnetic resonance apparatus 1, e.g. by a user, and/or results of the control device 9 such as e.g. image data can be displayed.

A method described herein can also be present in the form of a computer program product (e.g. a non-transitory computer-readable medium), which comprises a program and/or computer-readable and executable instructions to implement the aspects of the method described herein on the control device 9 when computer program product is executed on the control device 9 (e.g. via execution of the instructions by the computing unit 13).

Likewise, an electronically-readable data medium 26 with electronically-readable control information stored thereon can be present, which comprises at least one such computer program product just described and is designed in such a way that, when the data medium 26 is used in a control device 9 of a magnetic resonance apparatus 1, it carries out the aspects of the methods described herein.

The various functional blocks, apparatuses, modules, units, components of physical or functional units, etc., as shown in the drawings and described herein may be implemented unless otherwise noted via any suitable number and type of computer processors, hardware components, the execution of software algorithms, or combinations thereof, and thus may alternatively be referred to as a "unit," "system," "circuitry," or "device."

What is claimed is:

1. A method for acquiring data of an examination object using magnetic resonance (MR) imaging, comprising:
    loading a measurement protocol for acquiring data of an examination region of the examination object in at least two slices within a framework of a pulse sequence that is applied to the at least two slices in accordance with a predetermined chronological order of slice excitation;
    determining a time interval between excitations of spatially adjacent slices from among the at least two slices;
    determining a threshold time interval between excitations of spatially adjacent slices from among the at least two slices on the basis of parameters including (i) pulse sequence parameters, (ii) tissue parameters of the examination region of the examination object from which data is to be acquired within the framework of the pulse sequence, and (iii) selectable quality parameters;
    identifying time intervals between excitations of spatially adjacent slices from among the at least two slices that are less than the determined threshold time interval as time intervals to be adapted;
    adapting the identified time intervals to be adapted while maintaining the predetermined chronological order of slice excitation to generate adapted time intervals that are greater than or equal to the determined threshold time interval; and
    acquiring data of the examination object using an adapted pulse sequence that adheres to the adapted time intervals.

2. The method as claimed in claim 1, wherein the data of the examination region to be acquired is measured in turn and completely for each slice from among the at least two slices.

3. The method as claimed in claim 2, wherein adapting the identified time intervals to generate the adapted time intervals comprises inserting a wait time between two repetitions of the pulse sequence.

4. The method as claimed in claim 1, wherein the data of the examination region to be acquired is acquired at least partly within a repetition of the pulse sequence with an overall length of one repetition time.

5. The method as claimed in claim 4, wherein adapting the identified time intervals to generate the adapted time intervals comprises inserting a wait time within a repetition of the pulse sequence.

6. The method as claimed in claim 3, wherein adapting the identified time intervals to generate the adapted time intervals comprises inserting the wait time between two repetitions of the pulse sequence to lengthen the identified time intervals by the wait time so that at least one of the generated adapted time intervals is equal to the determined threshold time interval.

7. The method as claimed in claim 1, wherein determining the threshold time interval on the basis of the parameters includes using a maximum value for a longitudinal relaxation time T1 associated with tissue present in the examination region to be examined as at least one of the tissue parameters.

8. The method as claimed in claim 1, wherein the pulse sequence parameters used as the basis for the determination of the threshold time interval comprise a slice excitation profile of radio frequency (RF) excitation pulses used for excitation of the at least two slices.

9. The method as claimed in claim 1, wherein the selectable quality parameters used as the basis for the determination of the threshold time interval comprise a value for a maximum allowable pre-saturation of a magnetization of one of the at least two slices before excitation.

10. The method as claimed in claim 1, wherein the parameters used as the basis for the determination of the threshold time interval comprise further comprise user-selected parameters for the acquisition of data of the examination object.

11. The method as claimed in claim 1, wherein the parameters used as the basis for the determination of the threshold time interval are predetermined.

12. The method as claimed in claim 1, wherein the time interval between excitations of the spatially adjacent slices from among the at least two slices is different than a measurement time used for acquiring data of the examination object using the adapted pulse sequence.

13. The method as claimed in claim 12, wherein the measurement time comprises a repetition time multiplied by a number of echo signals to be recorded for one of the spatially adjacent slices.

14. The method as claimed in claim 1, wherein a length of a repetition time of the adapted pulse sequence spans multiple adjacent slices from among the at least two slices.

15. The method as claimed in claim 1, wherein the spatially adjacent slices from among the at least two slices are directly adjacent to one another, and
wherein the at least two slices are sequentially excited via the pulse sequence to acquire data of the examination region of the examination object as part of a sequential multi-slice (SMS) measurement.

16. The method as claimed in claim 1, wherein acquiring the data of the examination object using the adapted pulse sequence that adheres to the adapted time intervals reduces crosstalk artifacts compared to acquiring the data of the examination object using the pulse sequence without adapting the time intervals.

17. The method as claimed in claim 1, wherein the threshold time interval, unless exceeded, causes crosstalk artifacts in data of the examination object that is acquired using the pulse sequence.

18. The method as claimed in claim 1, wherein the threshold time interval, unless exceeded, causes crosstalk excitation effects in the spatially adjacent slices from among the at least two slices.

19. A magnetic resonance apparatus for acquiring data of an examination object using magnetic resonance (MR) imaging, comprising:
a magnet;
gradient circuitry;
radio frequency (RF) circuitry; and
a controller configured to:
load a measurement protocol for acquiring data of an examination region of the examination object in at least two slices within a framework of a pulse sequence generated by the RF circuitry that is applied to the at least two slices in accordance with a predetermined chronological order of slice excitation;
determine a time interval between excitations of spatially adjacent slices from among the at least two slices;
determine a threshold time interval between excitations of spatially adjacent slices from among the at least two slices on the basis of parameters including (i) pulse sequence parameters, (ii) tissue parameters of the examination region of the examination object from which data is to be acquired within the framework of the pulse sequence, and (iii) selectable quality parameters;
identify time intervals between excitations of spatially adjacent slices from among the at least two slices that are less than the determined threshold time interval as time intervals to be adapted;
adapt the identified time intervals to be adapted while maintaining the predetermined chronological order of slice excitation to generate adapted time intervals that are greater than or equal to the determined threshold time interval; and
acquire data of the examination object using an adapted pulse sequence that adheres to the adapted time intervals.

20. A non-transitory computer-readable medium having instructions stored thereon that, when executed by a controller associated with a magnetic resonance (MR) apparatus for acquiring data of an examination object using MR imaging, cause the MR apparatus to:
load a measurement protocol for acquiring data of an examination region of the examination object in at least two slices within a framework of a pulse sequence generated via radio frequency (RF) circuitry that is applied to the at least two slices in accordance with a predetermined chronological order of slice excitation;
determine a time interval between excitations of spatially adjacent slices from among the at least two slices;
determine a threshold time interval between excitations of spatially adjacent slices from among the at least two slices on the basis of parameters including (i) pulse sequence parameters, (ii) tissue parameters of the examination region of the examination object from which data is to be acquired within the framework of the pulse sequence, and (iii) selectable quality parameters;
identify time intervals between excitations of spatially adjacent slices from among the at least two slices that are less than the determined threshold time interval as time intervals to be adapted;
adapt the identified time intervals to be adapted while maintaining the predetermined chronological order of slice excitation to generate adapted time intervals that are greater than or equal to the determined threshold time interval; and
acquire data of the examination object using an adapted pulse sequence that adheres to the adapted time intervals.

* * * * *